United States Patent [19]

Harris et al.

[11] 4,022,887

[45] May 10, 1977

[54] CARIOSTATIC COMPOSITIONS AND METHOD OF APPLICATION

[75] Inventors: Robert S. Harris, Waban; Abraham E. Nizel, Newton Centre, both of Mass.

[73] Assignee: Massachusetts Institute of Technology, Cambridge, Mass.

[22] Filed: May 24, 1972

[21] Appl. No.: 256,470

Related U.S. Application Data

[63] Continuation of Ser. No. 39,167, May 20, 1970, abandoned, which is a continuation-in-part of Ser. No. 659,578, Aug. 10, 1967, abandoned, which is a continuation of Ser. No. 457,187, May 19, 1965, abandoned, which is a continuation of Ser. No. 219,120, Aug. 23, 1962, abandoned.

[52] U.S. Cl. .................................. 424/128; 424/57
[51] Int. Cl.$^2$ .......................................... A61K 5/00
[58] Field of Search ............................ 424/49–58, 424/128

[56] References Cited

UNITED STATES PATENTS

3,699,220  10/1972   Westrate et al. .................. 424/57

OTHER PUBLICATIONS

Manly et al., *J. Dental Research*, vol. 28, pp. 160–162 & 168, 1949.
Fosdick et al., *J. Dental Res.*, vol. 39, p. 638, 1960.
Ruf, *Mittaus Gebiete Lebensmitt u. Hyg.*, vol. 49, pp. 479–485, 1958.
Weisenberg, *Northwestern University Bulletin*, vol. 62, pp. 41–45, Feb. 26, 1962.
*International Association for Dental Research Abstracts*, Mar. 16–18, 1962, pp. 40 J 63.

*Primary Examiner*—Shep K. Rose
*Attorney, Agent, or Firm*—Dike, Bronstein, Roberts, Cushman & Pfund

[57] ABSTRACT

The use of edible cyclotriphosphates and cyclotetraphosphates as phosphorous supplements in diets effectively inhibit the development of caries. The compounds may be incorporated in candies, for example, caramels, they may also be imbedded in fat particles, which in turn are distributed throughout a food composition such as a cereal.

4 Claims, No Drawings

CARIOSTATIC COMPOSITIONS AND METHOD OF APPLICATION

This is a continuation of application Ser. No. 39,167 filed on May 20, 1970 which latter application was filed as a continuation-in-part application of application Ser. No. 659,578 filed on Aug. 10, 1967. Application Ser. No. 659,578 was filed as a continuation of application Ser. No. 457,187 filed May 19, 1965 as a continuation of application Ser. No. 219,120 filed Aug. 23, 1962. All of the applications that preceded this application are now abandoned.

This invention relates to improved food supplements and more particularly provides food supplements having improved cariostatic action and has an object to provide supplements for food and feed compositions having a greatly improved dental caries-inhibiting effect. It is well known that present day food refining methods in food preparation such as occurs in milling and refining of flour, for example, remove many of the essential elements that our predecessors used to get in their normal diet. Consequently, it has been the practice in modern times to restore the necessary constituents to the diet by their addition to various food products.

In recent years, much research work has been done on the effect of various elements in diets with respect to the cariostatic effects on teeth. Among findings made in that research was the observation that additions of phosphorus to the diet are effective in inhibiting dental caries. Without an adequate supply of phosphorus in the animal system, the teeth, especially immature teeth, are susceptible to dental caries. To get an adequate supply of phosphorus into the system the phosphorus must be in an assimilable form.

Although it has been established that phosphorus is essential in the diet to maintain caries-free teeth, it has also been found that the various assimilable sources of phosphorus are not equivalent for this purpose in that some sources when incorporated into the diet provide considerably more inhibition to the formation of dental caries, than do the others.

It is therefore an object of the invention to provide a means for minimizing dental caries, through the addition to the diet of safe, readily-assimilable compounds of phosphorus.

It is another object of this invention to provide a supplement to food products and feed compositions which provides improved protection against dental caries. It is a further object of this invention to provide a method for protecting teeth against dental caries. It is another object of this invention to provide improved food compositions containing at least a cariostatic amount of a soluble cyclic phosphate material. Other objects, advantages, and aspects of this invention will be apparent from a reading of the following description and the accompanying claims.

This invention provides a greatly improved phosphoruscontaining food supplement to human and animal food products. This phosphorus food supplement can be easily augmented with other essential elements to provide proper balance for ready assimilation by the human body and to supply deficiencies. The form of phosphorus used in the food supplement of this invention not only provides phosphorus but has the surprising advantage of providing greatly enhanced inhibition of cariogenic activity, i.e., this form of food-supplement phosphorus provides a much greater degree of protection against dental caries than any of the usual heretofore known phosphorus-containing food supplements, food additives, or ingredients.

Food supplements in the form of heterocyclic phosphorus and oxygen containing compounds have been found to be very effective as cariostatic agents when included in foods. The cyclic phosphates useful for providing the food-supplement form of phosphorus are exemplified by sodium cyclotriphosphate, and sodium cyclotetraphosphate. Other examples are potassium cyclotriphosphate, iron cyclotriphosphate, and calcium sodium cyclotriphosphate. The preparation of sodium cyclotriphosphate is described by R.N. Bell in *Inorganic Synthesis*, ed. L.F. Audrieth, McGraw-Hill Book Co., New York, 1950, Vol. 3, pp.103–106.

The form of phosphorus in a supplement to foods which provides these beneficial advantages is cyclic phosphate compounds of the formula

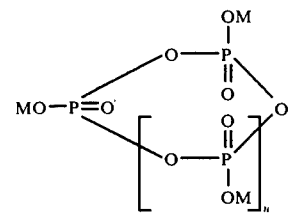

wherein M is an edible cation for use in human or animal food, n is a whole number integer of from 1 to 2, M can be, e.g., hydrogen, sodium, potassium, ammonium, calcium, magnesium or other cations which are essential, such as iron, cobalt, copper, maganese, etc. and mixtures thereof. The edible cations are those which are essential for nutritional balance or have no harmful effect when included in reasonable amounts in the diet. The differences provided by the phosphorus-containing food supplement of this invention are provided on the basis of the anion effect. The cation can be chosen on the basis of being edible and on its supplying nutritional balance, if desired.

This invention thus provides new food compositions having added thereto supplements which provide phosphorus in a highly cariostatic form. These supplements containing phosphorus in the form indicated above can be incorporated into the diet in a variety of ways: Conveniently, the phosphorus-containing food supplement containing the cyclic phosphate compound can be added into a component of the diet which is commonly eaten on a regular predictable basis. The cyclic phosphate can be physically mixed in with the food product, e.g., by blending, milling, etc., and is preferable incorporated into a stable item of normal diet. The food supplement may be loosely mixed in the food and it may be coated or uncoated. It can also be included in some liquid foods or feed products such as dietary formulas.

In one form which produces desirable results, the phosphorus compound is distributed throughout a lard fat which is then reduced to small particles before it is mixed with a cereal. The distribution of fat throughout the cereal and of phosphorus compound throughout the fat should be fine enough and complete enough so that the appearance and taste of the food is not impaired. Typical fats of this type are partially and fully hydrogenated oils, such as animal and vegetable oils. The fat is preferably one that is solid at room temperature, e.g., fats having a melting point of approximately 90° F or higher and therefore the size of the fat particles and the phosphorus in the fat can vary within wide limits depending on factors such as the nature of the final food mixture and the size and type of animal for which the food is intended.

The original purpose for using hard pearls of fat was a means of determining what mechanism was involved in cariostosis. The three mechanisms under consideration were topologic, local systemic (that is, by way of the saliva glands) and systemic. It was thought that the hard pearls of fat would not melt in one's mouth at normal body temperatures, thereby obviating topological effects and the phosphate would return to the mouth only after digestion. However, it was discovered that the pearls of fat lodged in the crevices of the teeth and the phosphate was gradually released, proving substantially more cariostatic than would otherwise be possible. In passing as a control mechanism, it was also found that the hard pearls of fat without phosphate were in fact cariogenic.

The amount of the food supplement cyclophosphate compound which is incorporated into a given amount of a diet will depend upon the food product to which it is added but generally quantities ranging from about 0.05% to 3% by weight of added phosphorus computed as the element are sufficient. Quantities on order of from 0.4% to 1% by weight, are preferred in many cases. Food containing the subject cariostatic composition can be included in daily meals or as often as thought necessary. Highly cariogenic diets with high incidence of caries would indicate greater usage.

When the food supplement is to blend with a relatively highly colored food, such as a cereal, it may be colored to correspond with that of the food. This may be achieved by adding a suitable food coloring to a slurry or solution of the food supplement during its preparation or it may be applied to the surface of the supplement in any convenient manner.

The cyclic phosphate compounds of the above described type up to now were seldom considered to be of any technological value. Except when M is hydrogen, they exhibited only the functions of salts of strong acids, i.e., they do not have any weakly acidic hydrogen ions as are present in other phosphate salts. For this reason, these salts were always considered to be in the same group as ordinary inorganic salts made from a strong base and a strong acid (such as sodium hydroxide and hydrochloric acid reacting to give sodium chloride) to give salts as $Na_2SO_4$, $NaNO_3$, etc. Furthermore, the cyclophosphates were also considered to be of little practical value in that they do not have strong sequestering or water-softening properties as do the chain phosphates. Neither do they possess the buffering action of the orthophosphates. It is considered surprising therefore to find that the cyclophosphates have advantages in their use in food product and feed composition supplements.

With them can be used cheap sources of calcium to obtain the proper Ca/P balance. Such calcium sources include calcium sulfate, calcium carbonate, and equivalent calcium salts. Also, phosphorus supplied in the manner of this inventions permits the supplying to the food product additional phosphorus without impairing the effects of other supplements. For example, in baked compositions if a leavening agent composition is supplied to the food product by means of a $Ca(HPO_4)_2$—$NaHCO_3$ mixture, the quantities of phosphorus in the baked food, such as bread, rolls, pastries, etc. can be increased without impairing leavening action by the use of the presently provided food supplements.

Food products enriched or fortified with the cyclophosphate supplements of the above defined types include cereal products derived from wheat, corn, rice, and oats in the form of flour, grits, or specialized articles such as breakfast cereals and prepared mixes. Also included are many other carbohydrate, proteinaceous, and fat-containing (lipids) food products such as heat treated or pasteurized dairy products, e.g., process cheeses, candies (especially sticky viscous types which normally tend to adhere to the teeth and dissolve slowly), and vitamin compositions, such as concentrates of vitamin B, C, D. The amount of elemental phosphate used will vary from about 0.05% to about 3% of the food product. The cyclophosphates described above in the form of the calcium and iron salts are useful for providing balanced food supplements. Calcium and iron supplements may also be provided in the form of salts thereof such as calcium carbonate and ferrous gluconate admixed with the cyclophosphate salts in a desired proportion to provide a balanced food supplement, e.g., as to provide about 2000 mg of calcium and 120 mg of iron per pound of cereal.

The use of these phosphates in candies, particularly viscous candies, surprisingly offsets the caries-producing effects of sugars in the candies. Typical candies in which the phosphates may be incorporated are caramels, chocolates, chocolate bars, gum drops, lozenges, hard tablets, etc. The phosphates are easily incorporated into the candies during any one of several stages of manufacture. It is only necessary to distribute the phosphates enough to insure against a concentration at any one point that would be likely to effect the palatability of the final product.

Caramel, being sticky and viscous at body temperatures, proved to be an excellent carrier. In one experiment, the caramel was frozen and then ground up before being fed to animals. It was there found that the cariostatic quality of the composition was reduced because the caramel did not stick to the teeth. It is quite apparent then that the oral clearance time is enhanced by the sticky quality of the candy, especially that of caramel.

EXAMPLE 1

A food supplement containing cyclotriphosphate neutralized with iron was prepared by passing a solution of sodium cyclotriphosphate through an ion-exchange column to remove sodium and then reacting the resulting acid with iron carbonate to form an iron salt of the cyclotriphosphate.

Food supplements containing cyclotriphosphate ions and a mixture of metal ions were also prepared by mixing iron and sodium trimetaphosphates in the desired proportions to form crystalline food supplements.

EXAMPLE 2

Food supplements containing calcium are prepared by combining calcium sodium cyclotriphosphate with sodium cyclotriphosphate to get a crystalline food supplement containing 5–20% calcium and 70–74% $P_2O_5$.

EXAMPLE 3

Potassium cyclotriphosphate was ground sufficiently to pass through a twenty mesh screen, then added with stirring to melted hydrogenated lard and chilled. The lard-imbedded phosphate was then comminuted to pass through a thirty mesh screen.

The compositions of the control caries-producing diet (No. 1) and the three experimental diest (Nos. 2, 3, 4) are shown in Table 1, wherein the figures are percentages of total composition based on weight. Diet No. 4 was prepared by adding sufficient lard-imbedded phosphorus to double the phosphorus content of the control diet from 0.4 percent to 0.8 percent. Diet No. 3 was made identical to diet No. 4 except that the phosphate and the granular lard were added separately. Diet No. 2 was supplemented with the same amount of lard as in diets No. 3 and 4, but with no phosphate, and served as a double control.

| Ingredients | No. 1 | No. 2 | No. 3 | No. 4 |
|---|---|---|---|---|
| Yellow maize (20 mesh) | 47.0 | 44.56 | 42.83 | 42.83 |
| Milk Solids (non-fat) | 20.0 | 18.96 | 18.96 | 18.96 |
| Sucrose | 14.0 | 13.27 | 13.27 | 13.27 |
| Plastic cream | 10.0 | 9.48 | 9.48 | 9.48 |
| Alfalfa meal | 6.0 | 5.69 | 5.69 | 5.69 |
| Liver concentrate | 2.0 | 1.90 | 1.90 | 1.90 |
| Sodium chloride | 1.0 | 0.95 | 0.95 | 0.95 |
| Hydrogenated lard | | 5.19 | 5.19 | |
| Potassium cyclotriphosphate | | | 1.73 | |
| Lard-imbedded potassium cyclotriphosphate | | | | 6.92 |

EXAMPLE 4

Lard-imbedded sodium cyclotriphosphate was added to a nutritionally complete diet for rats by mixing 1.3 parts by weight with 66.1 parts lactalbumin and 2.2 parts confectioners sugar. This mixture was then blended with a mixture of 4.7 cellulose, 1 part vitamin mixture and 3 parts mineral mixture. 3 parts cottonseed oil, diluted with 5 volumes ethyl alcohol to ensure distribution, was poured slowly into the mixture while it was being stirred vigorously. The composition is then fed to rats with distilled water, and caries development is later noted after autopsy.

EXAMPLE 5

Caramel containing 1.3 parts sodium cyclotriphosphate is prepared by adding the desired weight of the phosphate to the caramel during manufacture. It is fed to rats at a 67% level in a nutritionally complete diet, and caries development is noted after autopsy.

We claim:

1. A method of inhibiting caries in live human teeth which comprises orally administering to the human a non-toxic cariostatic amount of a cyclic phosphate of the formula

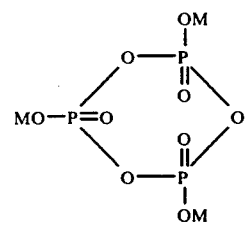

where M is sodium or potassium, in an ingestible carrier.

2. The method of claim 1 where the cariostatic amount of the cyclic phosphate is from 0.05 to 3% by weight computed as elemental phosphorus.

3. The method of claim 1 where the carrier is sticky and viscous.

4. The method of claim 1 where the carrier is a lard fat.

* * * * *